United States Patent
Sasaki et al.

(12)

(10) Patent No.: US 6,624,336 B1
(45) Date of Patent: Sep. 23, 2003

(54) PROCESS FOR PRODUCING TETRAFLUOROBENZENEMETHANOLS

(75) Inventors: Toru Sasaki, Fukushima (JP); Tetsuhiro Furukawa, Fukushima (JP); Toru Yoshida, Fukushima (JP); Yutaka Ohnishi, Kanagawa (JP); Hiroyuki Monzen, Kanagawa (JP); Hideo Miyata, Kanagawa (JP); Kohei Morikawa, Kanagawa (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 09/959,715

(22) PCT Filed: May 2, 2000

(86) PCT No.: PCT/JP00/02912
§ 371 (c)(1),
(2), (4) Date: Nov. 5, 2001

(87) PCT Pub. No.: WO00/68173
PCT Pub. Date: Nov. 16, 2000

Related U.S. Application Data

(60) Provisional application No. 60/136,403, filed on May 27, 1999, and provisional application No. 60/169,628, filed on Dec. 8, 1999.

(30) Foreign Application Priority Data

May 7, 1999 (JP) ............................................. 11-126777
Nov. 26, 1999 (JP) ............................................. 11-335869

(51) Int. Cl.$^7$ ............................................. C07C 33/46
(52) U.S. Cl. ........................ 568/812; 568/426; 568/436; 568/437; 568/592; 568/811
(58) Field of Search ................................. 568/426, 592, 568/811, 812, 436, 437

(56) References Cited

U.S. PATENT DOCUMENTS

| 4,183,950 A | * | 1/1980 | Naumann |
| 6,020,517 A | * | 2/2000 | Monzen |

FOREIGN PATENT DOCUMENTS

| EP | 302612 | 2/1989 |
| JP | 44-28493 | 11/1969 |
| JP | 63-39832 | 2/1988 |
| JP | 63-206491 | 8/1988 |
| JP | 1-119686 | 5/1989 |
| WO | 98/08795 | 3/1998 |

OTHER PUBLICATIONS

Chemical Abstracts, 1969, vol. 71, No. 23, the abstract No. 112563.

Vysochin, V. I., et al., "Reactions of pentafluorobenzaldehyde. II. Synthesis of derivatives of 2,3, 5, 6–tetrafluorobenzaldehyde from pentafluorobenzaldehyde", Zh. Obshch. Khim., 1969, vol. 39, No. 7, pp. 1607–1615.

* cited by examiner

*Primary Examiner*—Michael L. Shippen
(74) *Attorney, Agent, or Firm*—Sughrue Mion, PLLC

(57) ABSTRACT

The present invention relates to a process by a series of reactions using tetrafluorocyanobenzens as material for producing tetrafluorobenzenemethanols, tetrafluorobenzenecarbaldehyde dialkylacetals and tetrafluorobenzenecarbaldehydes in a high purity and a high yield which are useful as intermediates in the production of cyclopropanecarboxylic acid esters having insecticidal action, and also relates to a novel tetrafluorobenzenecarbaldehyde dimethylacetal.

17 Claims, No Drawings

US 6,624,336 B1

PROCESS FOR PRODUCING TETRAFLUOROBENZENEMETHANOLS

CROSS REFERENCE TO RELATED APPLICATIONS

This application is an application filed under 35 U.S.C. §111(a) claiming benefit pursuant to 35 U.S.C. §119(e) (1) of the filing dates of U.S. Provisional Application No. 60/136,403 filed May 27, 1999 and U.S. Provisional Application No. 60/169,628 filed Dec. 8, 1999 pursuant to 35 U.S.C. §111(b).

TECHNICAL FIELD OF THE INVENTION

The present invention relates to a process for producing tetrafluorobenzenemethanols represented by formula (4)

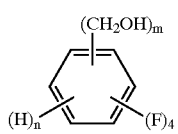

(wherein m represents 1 or 2, n represents 0 or 1, and m+n=2) useful as an intermediate of pesticide or medicine and a process for producing an intermediate in the production of the tetrafluorobenzenemethanols.

More specifically, the present invention relates to a process for producing tetrafluorobenzenemethanols, tetrafluorobenzenecarbaldehyde dialkylacetals and tetrafluorobenzenecarbaldehydes which are useful as intermediates in the production of cyclopropanecarboxylic acid esters having excellent insecticidal action by a series of reactions using tetrafluorocyanobenzene as a starting material, and also relates to a novel tetrafluorobenzenecarbaldehyde dimethylacetal.

BACKGROUND ART

It is known that 2,2-dimethyl-3-halogenovinyl-cyclopropanecarboxylic acid esters of a benzyl alcohol substituted by from 1 to 4 fluorines and from 0 to 2 chlorines have good insecticidal action (see, German Patent Publication (OLS) No. 2,658,074). In particular, it is known that cyclopropanecarboxylic acid esters of 2,3,5,6-tetrafluorobenzyl alcohol are an excellent insecticide because these have good insecticidal action but at the same time, are low in the toxicity to mammals as compared with cyclopropanecarboxylic acid esters of pentafluorobenzyl alcohol (see, German Patent Publication (OLS) No. 3,705,224).

With respect to the process for producing tetrafluorobenzenemethanol represented by formula (4), a method of reducing a halogen-substituted benzoic acid derivative by a metal hydride such as $NaBH_4$ and $LiAlH_4$ has been proposed.

For example, German Patent Publication (OLS) No. 3,714,602 discloses a method where 2,3,5,6-tetrafluorobenzoic acid is reacted with $NaBH_4$ and then treated with an alkylating agent to produce 2,3,5,6-tetrafluorobenzyl alcohol. German Patent Publication (OLS) Nos. 2,658,074, 2,714,042 and 2,661,074 disclose a method of reducing polyfluorobenzoyl fluoride by $NaBH_4$ to produce polyfluorobenzyl alcohol and a method of reducing polyfluorobenzoyl fluoride by $LiAlH_4$ to produce polyfluorobenzyl alcohol in which one or more fluorine substituent is defluorinated.

In British (Unexamined) Patent Publication No. 2,127,013, 2,3,5,6-tetrafluoroterephthaloyl chloride and $NaBH_4$ are reacted to produce 2,3,5,6-tetrafluorobenzenedimethanol.

Furthermore, in European (Unexamined) Patent Publication No. 31,199, 1,2,4,5-tetrafluorobenzene and n-butyl lithium are reacted, carbon dioxide is subsequently allowed to act thereon, thereby forming 2,3,5,6-tetrafluorobenzoic acid, and this is reduced by $LiAlH_4$ to produce 2,3,5,6-tetrafluorobenzyl alcohol.

These methods all use an expensive hydrogenated metal reagent in a stoichiometric amount and cannot be an industrially advantageous method.

In addition, for producing tetrafluorobenzenemethanol represented by formula (4), a method using an electrolytic reduction has also been proposed. For example, in JP-A-1-119686 (the term "JP-A" as used herein means an "unexamined published Japanese patent application"), pentafluorobenzoic acid is electrolytically reduced using a solid metal or solid alloy for the cathode and an aqueous solution of sulfuric acid, hydrochloric acid, phosphoric acid or sulfonic acid for the electrolytic solution, thereby producing 2,3,5,6-tetrafluorobenzyl alcohol together with 2,3,5,6-tetrafluorobenzaldehyde.

In JP-A-63-206491, a pentafluorobenzoic acid is electrolytically reduced using a solid metal or solid alloy for the cathode and a sulfuric acid aqueous solution for the electrolytic solution, thereby producing 2,3,5,6-tetrafluorobenzyl alcohol as a mixture with pentafluorobenzyl alcohol.

There have been proposed many other methods using electrolytic reduction, however, similarly to the above-described cases, a benzyl alcohol is produced as a mixture in all methods (see, *J. Electroanal. Chem.*, page 215 (1991), *J. Electroanal. Chem.*, page 315 (1987), *J. Chem. Soc. Perkin Trans I*, page 189 (1972), *J. Appl. Electrochem.*, page 1082 (1992), and *Denki Kagaku Oyobi Kogyo Butsuri Kagaku* (Electrochemistry and Industrial Physical Chemistry), page 83 (1990)).

In any of these methods, the yield is low and the purity of the product is not high. Particularly, pentafluorobenzyl alcohol from which cyclopropanecarboxylic acid ester harmful to human body is derived, cannot be prevented from mixing into the product.

In order to overcome these problems, International Patent Publication No. 9808795 has proposed a process for producing a fluorinated benzyl alcohol, where fluorinated dicyanobenzene is hydrogenolized in the presence of a catalyst, the cyano group only on one side is hydrodecyanated to produce fluorinated benzonitrile, and then the cyano group of the fluorinated benzonitrile is converted into a hydroxymethyl group. In this method, the conversion of cyano group into hydroxymethyl group is attained by a method of reducing the cyano group into an aldehyde group and reducing it into a hydroxymethyl group, a method of reducing the cyano group directly into a hydroxymethyl group, or a method of hydrolyzing the cyano group into a carboxyl group and then reducing the carboxyl group into a hydroxymethyl group.

However, some problems are present in the process of converting the cyano group into a hydroxymethyl group. To speak more specifically, in the method of hydrolyzing the cyano group into a carboxyl group and then reducing the carboxyl group into a hydroxymethyl group, an expensive hydrogenated metal reagent is used in a stoichiometric amount and therefore, this is not an industrially advantageous method. In the method of reducing the cyano group directly into a hydroxymethyl group, the reaction yield is generally low. And, in the method of reducing the cyano group into an aldehyde group and then reducing it into a hydroxymethyl group, 2,3,5,6-tetrafluorobenzyl alcohol is by-produced in the process of reducing the cyano group into an aldehyde group.

The 2,3,5,6-tetrafluorobenzyl alcohol is an objective component but remains in the distillation still at the purification of aldehyde by distillation because it has a high boiling point. Therefore, this side production of 2,3,5,6-tetrafluorobenzyl alcohol causes reduction in the yield. If the 2,3,5,6-tetrafluorobenzyl alcohol having a high boiling point is recovered by distillation together with aldehyde, impurities are mixed and the product is disadvantageously reduced in the purity.

Aldehyde is an intermediate product in the successive reaction for reducing the cyano group into hydroxymethyl group, accordingly, it is very difficult to suppress the generation of benzyl alcohol as a product due to the excessive reaction. In other words, in order to maximize the yield of aldehyde, the end point of reaction must be very strictly controlled. Furthermore, in any method, a reaction solvent, a co-catalyst such as carboxylic acid, and water are used each in a large amount, and this causes problems such as bad productivity, loss of solvent or the like, and increase in the load for recovery.

OBJECT OF THE INVENTION

Therefore, the object of the present invention is to provide industrially useful methods for manufacturing, in a high purity and a high yield, tetrafluorobenzenemethanols represented by formula (4) useful as an intermediate of pesticide or medicine and tetrafluorobenzenecarbaldehyde dialkylacetals and tetrafluorobenzenecarbaldehydes which are an intermediate in the production of the tetrafluorobenzenemethanols.

In particular, the object of the present invention is to provide a process for producing 2,3,5,6-tetrafluorobenzyl alcohol, 2,3,5,6-tetrafluorobenzaldehyde, 2,3,5,6-tetrafluorobenzenedimethanol, 2,3,5,6-tetrafluoroterephthalaldehyde, 2,3,5,6-tetrafluorobenzaldehyde dimethylacetal and 2,3,5,6-tetrafluoroterephthalaldehyde dimethylacetal, which are useful as an intermediate in the production of pyrethroids having good insecticidal action and low toxicity to human body, by an industrially advantageous method.

DISCLOSURE OF THE INVENTION

The present invention relates to a process for producing tetrafluorobenzenemethanols represented by formula (4), tetrafluorobenzenecarbaldehyde dialkylacetals represented by formula (2) and tetrafluorobenzenecarbaldehydes represented by formula (3) described in below (1) to (14), which are useful as an intermediate in the production of cyclopropanecarboxylic acid esters having excellent insecticidal action, by a series of reactions using tetrafluorocyanobenzene represented by formula (1) as a material. The present invention also relates to a novel tetrafluorobenzenecarbaldehyde dimethylacetal represented by formula (5).

(1) A process for producing a tetrafluorobenzenemethanol, comprising catalytically reducing a tetrafluorocyanobenzene represented by formula (1):

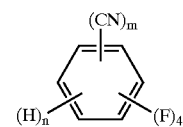

(1)

(wherein m represents 1 or 2, n represents 0 or 1, and m+n=2) in the presence of an alkyl alcohol represented by R—OH (wherein R represents an alkyl group having from 1 to 4 carbon atoms) and an acid to prepare a tetrafluorobenzenecarbaldehyde dialkylacetal represented by formula (2):

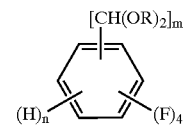

(2)

(wherein m and n have the same meanings as defined above), hydrolyzing it to prepare a tetrafluorobenzenecarbaldehyde represented by formula (3):

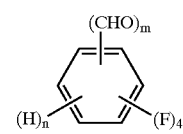

(3)

(wherein m and n have the same meanings as defined above), and reducing it to produce a tetrafluorobenzenemethanol represented by formula (4):

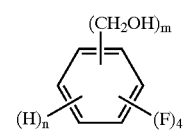

(4)

(wherein m and n have the same meanings as defined above).

(2) A process for producing a tetrafluorobenzenecarbaldehyde dialkylacetal represented by formula (2);

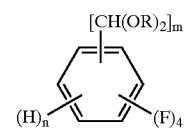

(2)

(wherein m and n have the same meanings as in above (1)) comprising catalytically reducing a tetrafluorocyanobenzene represented by formula (1)

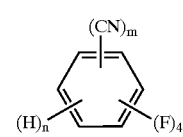

(1)

in the presence of an alkyl alcohol represented by R—OH (wherein R has the same meanings as defined in above (1)) and an acid.

(3) The process for producing a tetrafluorobenzenecarbaldehyde dialkylacetal as described in above 2, wherein the alkyl alcohol is methanol and the compound represented by formula (2) is tetrafluorobenzenecarbaldehyde dimethylacetal.

(4) The process for producing a tetrafluorobenzenecarbaldehyde dialkylacetal as described in above (2) or (3), wherein the catalyst used in the catalytic reduction is sponge nickel.

(5) The process for producing a tetrafluorobenzenecarbaldehyde dialkylacetal as described in any one of above (2) to (4), wherein copper, tin or zinc as a dissimilar metal component is added to the catalyst used in the catalytic reduction.

(6) The process for producing a tetrafluorobenzenecarbaldehyde dialkylacetal as described in any of above (2) to (5), wherein the catalytic reduction is carried out under condition that the amount of water present in the reaction is 1 time in mol or less based on the acetal group of tetrafluorobenzenecarbaldehyde dialkylacetal represented by formula (2).

(7) A process for producing a tetrafluorobenzenecarbaldehyde represented by formula (3)

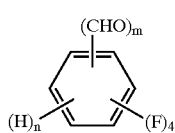

(3)

(wherein m and n have the same meanings as defined in above (1)), comprising hydrolyzing a tetrafluorobenzenecarbaldehyde dialkylacetal represented by formula (2)

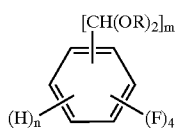

(2)

(wherein m and n have the same meanings as defined above).

(8) A process for producing a tetrafluorobenzenecarbaldehyde described in above (6) using fluorobenzenecarbaldehyde dialkylacetal represented by formula (2)

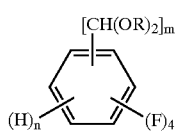

(2)

obtained by catalytically reducing a tetrafluorocyanobenzene represented by formula (1)

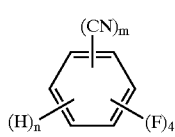

(1)

(wherein m and n have the same meanings as defined in above (1)) in the presence of an alkyl alcohol represented by R—OH (wherein R has the same meanings as defined in above (1)) and an acid.

(9) The process for producing a tetrafluorobenzenecarbaldehyde as described in above (7) or (8), wherein water is added and then the hydrolysis is performed while separating an alkyl alcohol by distillation.

(10) The process for producing a tetrafluorobenzenecarbaldehyde as described in any of above (7) to (9), wherein water in excess amount of 10 times in mol or more is used based on the acetal group of tetrafluorobenzenecarbaldehyde dialkylacetal represented by formula (2).

(11) The process for producing a tetrafluorobenzenecarbaldehyde as described in any one of (7) to (9), wherein the tetrafluorobenzenecarbaldehyde dialkylacetal represented by formula (2) is 2,3,5,6-tetrafluorobenzaldehyde dialkylacetal or 2,3,5,6-tetrafluoroterephthalaldehyde dialkylacetal, and the tetrafluorobenzenecarbaldehyde represented by formula (3) is corresponding 2,3,5,6-tetrafluorobenzaldehyde or 2,3,5,6-tetrafluoroterephthalaldehyde.

(12) A process for producing a tetrafluorobenzenemethanol represented by formula (4),

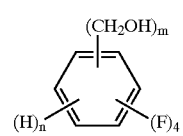

(4)

(wherein m and n have the same meanings as defined above) comprising reducing a tetrafluorobenzenecarbaldehyde represented by formula (3)

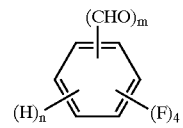

(3)

(wherein m and n have the same meanings as defined above), prepared by hydrolyzing a tetrafluorobenzenecarbaldehyde dialkylacetal represented by formula (2)

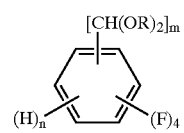

(2)

(wherein m and n have the same meanings as defined above).

(13) The process for producing a tetrafluorobenzenemethanol as described in above (12), wherein the tetrafluorobenzenecarbaldehyde dialkylacetal represented by formula (2) is 2,3,5,6-tetrafluorobenzaldehyde dialkylacetal or 2,3,5,6-tetrafluoroterephthalaldehyde dialkylacetal, the tetrafluorobenzenecarbaldehyde represented by formula (3) is corresponding 2,3,5,6-tetrafluorobenzaldehyde or 2,3,5,6-tetrafluoroterephthalaldehyde, and the tetrafluorobenzenemethanol represented by formula (4) is corresponding 2,3,5,6-tetrafluorobenzyl alcohol or 2,3,5,6-tetrafluorobenzenedimethanol.

(14) Tetrafluorobenzenecarbaldehyde dimethylacetals represented by formula (5)

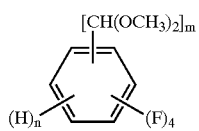

(5)

(wherein m and n have the same meanings as defined in above (1)).

MODE FOR CARRYING OUT THE INVENTION

The present invention is described in detail below. A series of reactions in the present invention is shown in reaction formula below.

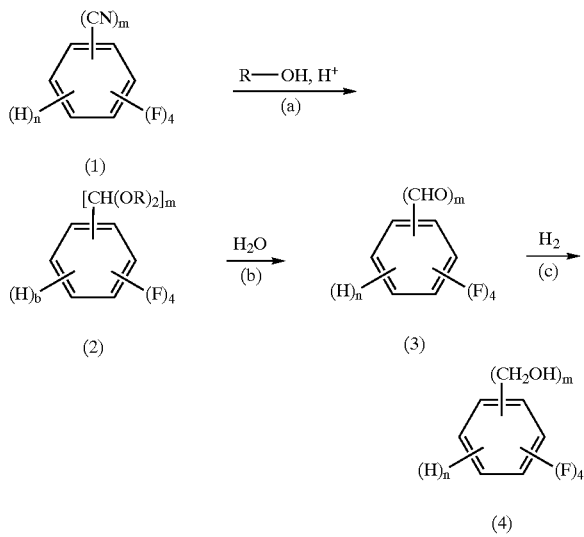

In the reaction formula, R represents an alkyl group having from 1 to 4 carbon atoms and m represents 1 or 2, n represents 0 or 1, and m+n=2.

In the present invention, a tetrafluorocyanobenzene represented by formula (1) is used as a reaction starting material and the catalytic reduction reaction is performed in the presence of a specific alkyl alcohol and an acid in step (a), whereby a tetrafluorobenzenecarbaldehyde dialkylacetal represented by formula (2) is produced. Subsequently, in step (b), water is added to perform the hydrolysis, as a result, a tetrafluorobenzenecarbaldehyde represented by formula (3) can be produced. Next, by using highly pure tetrafluorobenzenecarbaldehyde obtained from step (b) or its aldehyde as material, tetrafluorobenzenemethanols can be produced in a high yield by an industrially useful method in step (c) without using a large amount of an expensive hydrogenated metal reagent.

As prior art related to the reaction used in the steps of the present invention, a method of hydrogenating pentafluorobenzonitrile using sponge nickel in the presence of a sulfuric acid and an alcohol to produce a pentafluorobenzaldehyde dialkylacetal, is disclosed in JP-A-63-39832 which comprises a reaction similar to the one in step (a) for converting a nitrile group into an acetal group.

As an example of the reaction for converting an acetal group into an aldehyde group in step (b), it is reported that 2,3,5,6-tetrafluorobenzaldehyde could be obtained by the hydrolysis of 2,3,5,6-tetrafluorobenzaldehyde diethylacetal synthesized starting from pentafluorobenzonitrile through a reaction with $LiAlH_4$, though the yield is as low as 34% (see, J. General Chem. USSR, Vol. 39, No. 7, page 1576 (1969)).

The tetrafluorobenzenecarbaldehyde dialkylacetals represented by formula (2) can be produced according to step (a) of the present invention. Preferred examples include tetrafluorobenzaldehyde dimethylacetal and tetrafluoroterephthalaldehyde dimethylacetal.

As analogous compounds of the compound obtained by step (a), pentafluorobenzaldehyde dialkylacetal (see, JP-A-63-39832) and tetrafluorobenzaldehyde diethylacetal (see, J. General Chem. USSR, Vol. 39, No. 7, page 1576 (1969)) are known. However, no report is known on the tetrafluorobenzaldehyde dimethylacetal. Tetrafluorobenzaldehyde dimethylacetal is a novel and industrially very useful compound.

Specific examples of the tetrafluorocyanobenzene represented by formula (1) used as the starting material in the present invention include 2,3,5,6-tetrafluorobenzonitrile, 2,3,4,5-tetrafluorobenzonitrile, 2,3,4,6-tetrafluorobenzonitrile, 2,3,5,6-tetrafluoroterephthalonitrile, 2,3,4,5-tetrafluorophthalonitrile and 2,3,4,6-tetrafluoroisophthalonitrile.

Among these, 2,3,5,6-tetrafluorobenzonitrile and 2,3,5,6-tetrafluoroterephthlonitrile are preferred.

Of these compounds, tetrafluorodicyanobenzenes can be produced, for example, by replacing the chlorine atom of a tetrachlorodicyanobenzene obtained as a result of chlorination of a dicyanobenzene, with fluorine of an alkaline fluoride. Specifically, JP-B-44-28493 (the term "JP-B" as used herein means an "examined Japanese patent publication") discloses a method of reacting 2,3,5,6-tetrachloroterephthalonitrile with potassium fluoride to produce 2,3,5,6-tetrafluoroterephthalonitrile. The tetrafluorobenzonitrile can be produced by a method disclosed, for example, in International Patent Publication No. 9808795, a method of hydrogenolizing a fluorinated dicyanobenzene and thereby hydrodecyanating the cyano group only on one side.

Use of tetrafluorobenzonitrile obtained by the process of the present invention is advantageous particularly in the production of 2,3,5,6-tetrafluorobenzaldehyde dialkylacetal. The reason is that 2,3,5,6-tetrafluorobenzyl alcohol produced starting from this acetal is completely free of pentafluorobenzyl alcohol which may work out to a starting material of pyrethroids highly toxic to mammals.

As the catalyst used in the catalytic reduction in step (a), a metal catalyst such as nickel, palladium, platinum, ruthenium, cobalt or copper, may be used. Among these, a nickel catalyst is preferred. The catalyst may be a metal as it is or in the form of a supported catalyst. As the supporter, activated carbon, silica, alumina or the like may be used. Specific examples of preferred catalysts include sponge nickel catalyst. The amount of the catalyst added is not particularly limited, however, the catalyst is preferably used in an amount of 1 mass % or more based on the tetrafluorocyanobenzene represented by formula (1).

Also, it is effective to add a dissimilar metal component to the catalyst. To this purpose, copper, tin, chromium, lead, cadmium, antimony, bismuth, molybdenum, zinc, iron or the like may be added as an element or as salt thereof and among these, copper, lead, or zinc component is preferred. The amount of the dissimilar metal added to the catalyst is preferably 0.1 to 50 mass % based on the catalyst.

Examples of the acid for use in reaction in step (a) include sulfuric acid, hydrochloric acid, phosphoric acid, formic acid, acetic acid, monochloroacetic acid, dichloroacetic acid and trifluoroacetic acid. Among these, sulfuric acid, hydrochloric acid and phosphoric acid are preferred.

The amount of the acid used is not particularly limited, however, the acid is preferably used in an amount of 1 times in mol or more based on the tetrafluorocyanobenzene represented by formula (1).

The alkyl alcohol represented by R—OH wherein R represents an alkyl group having from 1 to 4 carbon atoms in the present invention includes an alkyl alcohol having from 1 to 4 carbon atoms. Specific examples thereof include methanol, ethanol, 2-propanol and n-butanol. Among these, methanol is most preferred.

Alcohol is preferably used 2 times in mol or more, more preferably 10 times in mol or more, based on the tetrafluorocyanobenzene represented by formula (1).

In step (a), a solvent is not indispensable, however, a solvent such as hydrocarbon (e.g., toluene, ethyl benzene), an ether (e.g., 1,4-dioxane, tetrahydrofuran), dimethyl folmamide (DMF), dimethyl sulfoticido (DMSO) or sulfolane, may also be used.

The reaction temperature is not particularly limited. However, the reaction is preferably performed at a temperature of from 0° C. to around 100° C.

The method for supplying hydrogen is not particularly limited and the hydrogen may be blown into the reaction solution or may be passed through or intermittently supplied to the vapor phase moiety. The hydrogen may also be supplied as a mixed gas together with an inert gas such as nitrogen. The hydrogen partial pressure may be from reduced pressure to applied pressure.

If water is present in the reaction of step (a), it is usually undesirable because the tetrafluorobenzenecarbaldehyde dialkylacetal is disadvantageously converted into tetrafluorobenzenecarbaldehyde or the like due to hydrolysis. However, small amount of water does not matter which exists in sponge nickel prepared as water suspension. It was proved that the water does not adverse the reaction result of reaction in step (a) as long as the amount of water is as small as 1 times in mol or less based on the acetal group.

It is effective to perform a heat treatment after the tetrafluorocyanobenzene represented by formula (1) as a starting material is consumed in reaction of step (a). The heat treatment enables to increase the yield of the tetrafluorobenzenecarbaldehyde dialkylacetal represented by formula (2). The heat treatment is preferably performed at a temperature of from 40° C. to around 100° C. for 0.1 hour to 24 hours.

In the present invention, the tetrafluorobenzenecarbaldehyde dialkylacetal represented by formula (2) obtained by step (a) may be purified by distillation, extraction, two-layer separation or the like, or may be used in the subsequent hydrolysis reaction of reaction step (b) without passing through any particular purification. Or the tetrafluorobenzenecarbaldehyde dialkylacetal may be used as a mixture with tetrafluorobenzenecarbaldehyde represented by formula (3).

The end point of reaction in step (a) may be set at the point when hydrogen corresponding to 1 mol based on the cyano group of tetrafluorocyanobenzene is consumed or may be determined by measuring the amount of starting material consumed using an analysis instrument such as gas chromatography or by performing quantitative analysis of the amount of tetrafluorobenzenecarbaldehyde dialkylacetal represented by formula (2) or tetrafluorobenzenecarbaldehyde represented by formula (3) produced. Here, according to the process of the present invention, it is confirmed that in reaction of step (a), the yield does not decrease due to the decomposition or the like of product even if the reaction time is excessively prolonged.

The tetrafluorobenzenecarbaldehyde dialkylacetal represented by formula (2) obtained by step (a) is hydrolyzed according to step (b) and thereby converted into tetrafluorobenzenecarbaldehyde represented by formula (3).

In the acetalization shown in step (a), tetrafluorobenzenecarbaldehyde monoalkylacetal is produced in some cases but is similarly converted into tetrafluorobenzenecarbaldehyde by the hydrolysis.

The reaction in step (b) may be performed in the presence of an acid. The acid used in this reaction is sulfuric acid, hydrochloric acid, phosphoric acid, formic acid, acetic acid, monochloroacetic acid, dichloroacetic acid or trifluoroacetic acid, preferably sulfuric acid, hydrochloric acid or phosphoric acid. The amount of acid to be used is not particular limited. In step (b), a method of continuously using the acid used in step (a) is preferably used.

The amount of water added in step (b) is not particularly limited as long as it is 1 time in mol or more based on the acetal group of tetrafluorobenzenecarbaldehyde alkylacetal represented by formula (2) produced. However, since the reaction in step (b) is an equilibrium reaction, excess water of 10 times in mol or more is preferably used, so that the tetrafluorobenzenecarbaldehyde represented by formula (3) can be efficiently obtained in a high yield and a high purity.

In step (b), a solvent is not essential, however, a solvent such as hydrocarbon (e.g., toluene, ethylbenzene), an ether (e.g., 1,4-dioxane, tetrahydrofuran), DMF, DMSO or sulfolane may also be used.

The reaction temperature is not particularly limited but the reaction is preferably performed at a temperature of from 0° C. to around 200° C.

In step (b), when the alcohol contained and the alcohol produced by the reaction are removed by distillation, the equilibrium is shifted to the production side. By this so-called reactive distillation, the tetrafluorobenzenecarbaldehyde dialkylacetal represented by formula (2) contained can be efficiently converted into tetrafluorobenzenecarbaldehyde represented by formula (3). By this reactive distillation, the equilibrium is effectively shifted to the production side, so that the amounts of acid and water used in the hydrolysis reaction in step (b) can be greatly reduced.

In performing the reactive distillation, methanol is most preferably used as the alcohol. Methanol is inexpensive and has a low boiling point (64.7° C.), therefore, it can be easily distilled off and the hydrolysis reaction in step (b) can be efficiently accelerated. Furthermore, methanol does not form an azeotropic mixture with water and therefore, water can be prevented from distilling, so that the reaction of step (b) can be accelerated and at the same time, the recycle use of alcohol can be facilitated.

The tetrafluorobenzenecarbaldehyde represented by formula (3) obtained by step (b) can be purified by distillation, extraction, two-layer separation or the like. Among these, distillation is the most suitable method, in which a high purity tetrafluorobenzenecarbaldehyde can be obtained.

The tetrafluorobenzenecarbaldehyde is distilled out as a two-layer fraction with water. By separating the fraction into two layers, high-purity tetrafluorobenzenecarbaldehyde can be obtained. The tetrafluorobenzenecarbaldehyde dissolved in the aqueous layer can be recovered by the extraction using an organic solvent. The extraction solvent is not particularly limited but an aromatic hydrocarbon such as toluene is preferably used. The aqueous layer obtained may also be recycled as the water added in the hydrolysis in step (b) without extracting the tetrafluorobenzenecarbaldehyde in the aqueous layer. By this recycle use, not only the yield of tetrafluorobenzenecarbaldehyde is increased but also the amount of waste water treated can be greatly reduced.

By reducing the tetrafluorobenzenecarbaldehyde produced in step (b) represented by formula (3) according to step (c), a tetrafluorobenzenemethanol represented by formula (4) can be produced.

In the reaction of step (c), a metal catalyst such as nickel, palladium, platinum, ruthenium, cobalt, copper or the like is used. Among these, a nickel catalyst is preferred. It is also effective to add a dissimilar metal to the catalyst and to this effect, copper, tin, chromium, lead, cadmium, antimony, bismuth, zinc, iron or the like is added. The catalyst may be a metal as it is or in the form of a supported catalyst. As the supporter, activated carbon, silica, alumina or the like may be used. Specific examples of preferred catalysts include sponge nickel catalyst. A method of reducing aldehyde into an alcohol using a metal hydride such as $NaBH_4$ or $LiAlH_4$ may also be used.

A solvent is not essential in the reaction of step (c), however, a hydrocarbon such as toluene and ethyl benzene, an alcohol such as methanol, ethanol and 2-propanol, an ether such as 1,4-dioxane and tetrahydrofuran, or a carboxylic acid such as acetic acid and formic acid may be used as a solvent. Among these, an aromatic hydrocarbon such as toluene and ethyl benzene is preferred.

The reaction form is not particularly limited, however, a catalyst suspension flowing system, a fixed bed flowing system, a trickle bed or a batch system may be used.

The reaction temperature is not particularly limited, however, the reaction is preferably performed at a temperature of from ordinary temperature to around 200° C. With respect to the reaction pressure, the reaction may be performed under a pressure of from atmospheric pressure to applied pressure. The hydrogen partial pressure in the hydrogen reduction is not particularly limited but it is preferably 1 MPa or less.

The tetrafluorobenzenemethanol represented by formula (4) obtained by step (c) may be purified by distillation, extraction or two-layer separation after the catalyst is separated by an operation such as filtration, centrifugation or precipitation.

BEST MODE FOR CARRYING OUT THE INVENTION

The present invention is described below by referring to the Examples and Comparative Examples. The scope of the present invention is by no means limited to these Examples.

EXAMPLE 1

Preparation of 2,3,5,6-Tetrafluorobenzaldehyde Dimethylacetal

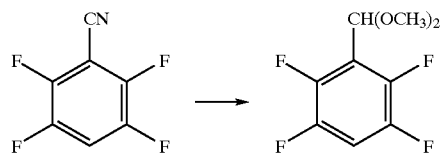

To a 50 ml-volume glass-made reactor equipped with a condenser tube, 0.50 g of sponge nickel thoroughly replaced by methanol was added and then a mixed solution containing 3.53 g of 2,3,5,6-tetrafluorobenzonitrile, 4.08 g of 97% sulfuric acid and 19.78 g of methanol was added. After the vapor phase moiety was thoroughly purged with hydrogen gas, a balloon charged with hydrogen gas was fixed to the top of the condenser tube and the solution was stirred at 10° C. for 6 hours. The reaction solution was analyzed by gas chromatography and the conversion of 2,3,5,6-tetrafluorobenzonitrile was found to be 65.9%. Subsequently, the solution was stirred at 25° C. overnight. Then, the conversion was 100%. From this reaction solution, the catalyst was filtered and after heating the filtrate at 60° C. for 2 hours, the methanol was distilled off. The residue was cooled to room temperature and 2.09 g of an oil layer comprising 2,3,5,6-tetrafluorobenzaldehyde dimethylacetal was separated. The oil layer was analyzed by means of a gas chromatograph, as a result, 2,3,5,6-tetrafluorobenzaldehyde dimethylacetal accounted for the area in percentage of 97.0% and the remaining was 2,3,5,6-tetrafluorobenzaldehyde. The 2,3,5,6-tetrafluorobenzaldehyde dimethylacetal was identified by NMR and mass spectrometry.

NMR ($CDCl_3$, δ): 3.50 (6H, s), 5.65 (1H, s), 7.19 (1H, m)
MASS: $M^+224$

EXAMPLE 2

Preparation of 2,3,5,6-Tetrafluorobenzaldehyde

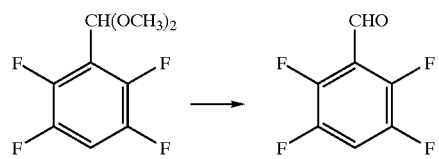

To a 200 ml-volume glass-made reactor equipped with a condenser tube, 2.09 g of 97% 2,3,5,6-tetrafluorobenzaldehyde dimethylacetal was added and subsequently 25.29 g of water and 45.72 g of 97% sulfuric acid were added. The mixture solution was stirred at 25° C. for 1 hour and thereafter, 100 ml of methylene chloride was added to separate the organic layer. The methylene chloride was distilled off by a rotary evaporator and the residue was cooled to obtain 1.67 g of crystal. The crystal was analyzed by means of a gas chromatograph as an internal standard method using o-dichlorobenzene and this compound was found to be 2,3,5,6-tetrafluorobenzaldehyde having a purity of 99.8%. The yield of 2,3,5,6-tetrafluorobenzaldehyde produced from 2,3,5,6-tetrafluorobenzaldehyde dimethylacetal was 99.6%.

EXAMPLE 3

Preparation of 2,3,5,6-Tetrafluorobenzaldehyde

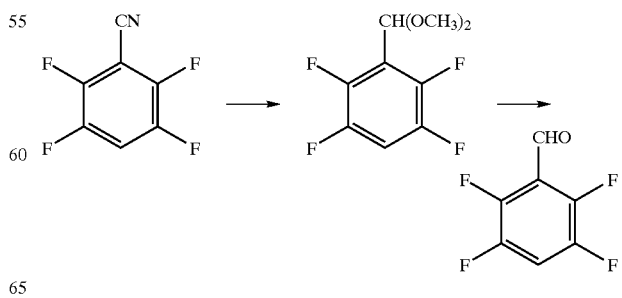

Into a 1 L-volume glass-made reactor equipped with a condenser tube, 127.08 g of 2,3,5,6-tetrafluorobenzonitrile and 120.00 g of methanol were charged. While stirring the mixture in a water bath, a mixed solution containing 228.48 g of methanol and 146.88 g of 97% sulfuric acid was added dropwise. Subsequently, 9.33 g of sponge nickel thoroughly replaced with methanol was added, the vapor phase moiety was thoroughly purged with hydrogen gas, and then the solution was stirred at 20° C. for 6 hours under atmospheric pressure in a hydrogen atmosphere. The reaction solution was analyzed by means of a gas chromatograph and it was found that 2,3,5,6-tetrafluorobenzonitrile completely disappeared. Thereafter, the vapor phase moiety was purged with nitrogen gas and the solution was stirred at 60° C. for 3 hours. The resulting reaction solution was analyzed by means of a gas chromatograph and it was confirmed that 2,3,5,6-tetrafluorobenzaldehyde dimethylacetal was mainly produced. After methanol was distilled off from the reaction solution, 660.22 g of water was added and the resulting solution was distilled under ordinary pressure. After cutting the first fraction containing methanol generated by the hydrolysis reaction of 2,3,5,6-tetrafluorobenzaldehyde dimethylacetal, 384.71 g of main fraction was allowed to distill. After standing at room temperature, the main fraction split into two layers of oil layer and aqueous layer. Thereafter, 103.65 g of oil layer was separated and cooled, then, the oil layer was crystallized. The crystal obtained was analyzed by means of a gas chromatograph as an internal standard method using o-dichlorobenzene and this compound was found to be 2,3,5,6-tetrafluorobenzaldehyde having a purity of 99.9%. In the analysis of gas chromatography, other impurities were not detected at all. The yield of 2,3,5,6-tetrafluorobenzaldehyde from 2,3,5,6-tetrafluorobenzonitrile was 80.1%. Also, the aqueous layer was analyzed by means of a gas chromatography and it was found that 4.52 g of 2,3,5,6-tetrafluorobenzaldehyde was dissolved therein (corresponding to a yield of 3.5% as calculated from 2,3,5,6-tetrafluorobenzonitrile).

EXAMPLE 4

Preparation of 2,3,5,6-Tetrafluorobenzaldehyde

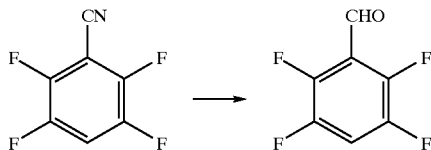

Into a 2 L-volume glass-made reactor equipped with a condenser tube, 127.08 g of 2,3,5,6-tetrafluorobenzonitrile and 468.48 g of methanol were charged. While stirring the mixture in a water bath, a mixed solution containing 228.48 g of methanol and 146.88 g of 97% sulfuric acid was added dropwise. Subsequently, 9.33 g of sponge nickel thoroughly replaced with methanol was added, the vapor phase moiety was thoroughly purged with hydrogen gas, and then the solution was stirred at 20° C. for 2 hours under atmospheric pressure in a hydrogen atmosphere. The resulting reaction solution was treated through the same operation as in Example 3. After the distillation, 101.59 g of 2,3,5,6-tetrafluorobenzaldehyde having a purity of 99.9% was obtained as the main fraction oil layer (yield based on 2,3,5,6-tetrafluorobenzonitrile: 78.5%).

Furthermore, it was found that 4.50 g of 2,3,5,6-tetrafluorobenzaldehyde was dissolved in the aqueous layer (yield based on 2,3,5,6-tetrafluorobenzonitrile: 3.5%).

EXAMPLE 5

Preparation of 2,3,5,6-Tetrafluorobenzaldehyde

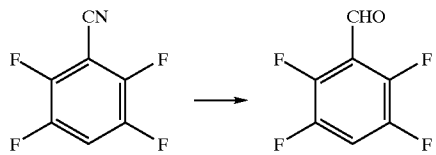

The same operation as in Example 4 was performed except for changing the temperature at the stirring in a hydrogen atmosphere to 10° C. After the distillation, 101.43 g of 2,3,5,6-tetrafluorobenzaldehyde having a purity of 99.9% was obtained as the main fraction oil layer (yield based on 2,3,5,6-tetrafluorobenzonitrile: 78.4%).

Furthermore, it was found that 4.54 g of 2,3,5,6-tetrafluorobenzaldehyde was dissolved in the aqueous layer (yield based on 2,3,5,6-tetrafluorobenzonitrile: 3.5%).

EXAMPLE 6

Preparation of 2,3,5,6-Tetrafluorobenzaldehyde

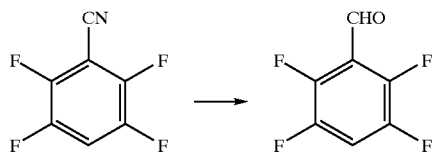

The same operation as in Example 4 was performed except for changing the temperature at the stirring in a hydrogen atmosphere to 30° C. After the distillation, 101.47 g of 2.3,5,6-tetrafluorobenzaldehyde having a purity of 99.9% was obtained as the main fraction oil layer (yield based on 2,3,5,6-tetrafluorobenzonitrile: 78.4%).

Furthermore, it was found that 4.50 g of 2,3,5,6-tetrafluorobenzaldehyde was dissolved in the aqueous layer (yield based on 2,3,5,6-tetrafluorobenzonitrile: 3.5%).

EXAMPLE 7

Preparation of 2,3,5,6-Tetrafluorobenzaldehyde

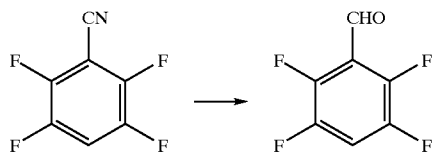

The same operation as in Example 3 was performed except for using 9.33 g of sponge nickel having a water content of 6.83 g. Before the distillation, the main products of the reaction solution were 2,3,5,6-tetrafluorobenzaldehyde and 2,3,5,6-tetrafluorobenzaldehyde dimethylacetal. After the distillation, 104.29 g of 2,3,5,6-tetrafluorobenzaldehyde having a purity of 99.9% was obtained as the main fraction oil layer (yield based on 2,3,5,6-tetrafluorobenzonitrile: 80.6%).

Furthermore, it was found that 4.40 g of 2,3,5,6-tetrafluorobenzaldehyde was dissolved in the aqueous layer (yield based on 2,3,5,6-tetrafluorobenzonitrile: 3.4%).

EXAMPLE 8

Preparation of 2,3,5,6-Tetrafluorobenzaldehyde

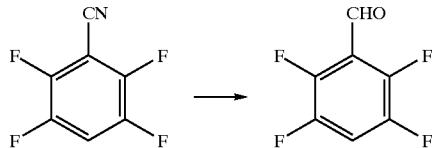

127.08 g of 2,3,5,6-tetrafluorobenzonitrile and 120.00 g of methanol were charged into a 1 L-volume glass-made reactor equipped with a condenser tube. While stirring the mixture in a water bath, a mixture solution containing 228.4 g of methanol and 146.88 g of 97% sulfuric acid was added dropwise. Subsequently, 9.33 g of sponge nickel thoroughly replaced with methanol was added, the vapor phase moiety was purged with hydrogen gas, and then the mixed solution was stirred at 20° C. for 6 hours under atmospheric pressure while continuously supplying hydrogen. The reaction solution was analyzed by means of a gas chromatograph and it was found that 2,3,5,6-tetrafluorobenzonitrile completely disappeared. While further continuously supplying hydrogen, the solution was stirred at 20° C. for 12 hours. The resulting reaction solution was analyzed by means of a gas chromatograph and it was confirmed that 2,3,5,6-tetrafluorobenzyl alcohol was not produced at all.

Thereafter, the reaction solution was treated by the same operation as in Example 2. After the distillation, 105.76 g of 2,3,5,6-tetrafluorobenzaldehyde having a purity of 99.9% was obtained as the main fraction oil layer.

Furthermore, it was found that 4.27 g of 2,3,5,6-tetrafluorobenzaldehyde was dissolved in the aqueous layer. The yield in total of oil layer and aqueous layer based on 2,3,5,6-tetrafluorobenzonitrile was 84.3%.

The yield of this Example is not greatly different from the yield of Example 2 and this reveals that even if the hydrogenation reaction time was excessively prolonged in this Example, the decrease in the yield due to the decomposition or the like of product does not occur.

EXAMPLE 9

Preparation of 2,3,5,6-Tetrafluorobenzaldehyde

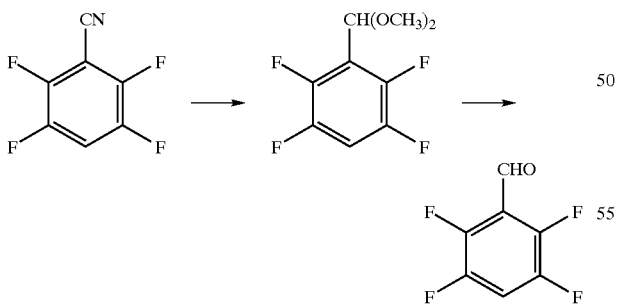

The same operation as in Example 3 was performed except for using a catalyst prepared by charging 12.39 g of sponge nickel and 14.36 g of a 10% cupric sulfate solution into a 500 ml-volume glass-made reactor equipped with a condenser tube and after stirring the solution for 30 minutes, removing the supernatant. Before the distillation, the main products of the reaction solution were 2,3,5,6-tetrafluorobenzaldehyde and 2,3,5,6-tetrafluorobenzaldehyde dimethylacetal. After the distillation, 110.7 g of 2,3,5,6-tetrafluorobenzaldehyde having a purity of 99.9% was obtained as the main fraction oil layer (yield based on 2,3,5,6-tetrafluorobenzonitrile: 85.6%).

Furthermore, it was found that 4.50 g of 2,3,5,6-tetrafluorobenzaldehyde was dissolved in the aqueous layer (yield based on 2,3,5,6-tetrafluorobenzonitrile: 3.5%).

EXAMPLE 10

Preparation of 2,3,5,6-Tetrafluorobenzaldehyde

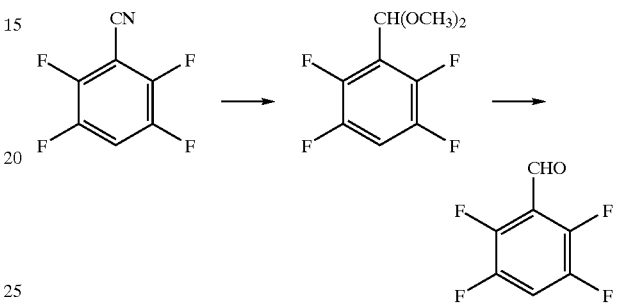

The same operation as in Example 9 was performed except for using 1.74 g of stannous sulfate and 12.39 g of sponge nickel having a water content of 6.96 g, and changing the time at the stirring in a hydrogen atmosphere to 7 hours. Before the distillation, the main products of the reaction solution were 2,3,5,6-tetrafluorobenzaldehyde and 2,3,5,6-tetrafluorobenzaldehyde dimethylacetal. After the distillation, 109.33 g of 2,3,5,6-tetrafluorobenzaldehyde having a purity of 99.9% was obtained as the main fraction oil layer (yield based on 2,3,5,6-tetrafluorobenzonitrile: 84.6 %).

Furthermore, it was found that 4.20 g of 2,3,5,6-tetrafluorobenzaldehyde was dissolved in the aqueous layer (yield based on 2,3,5,6-tetrafluorobenzonitrile: 3.3%).

EXAMPLE 11

Preparation of 2,3,5,6-Tetrafluorobenzaldehyde

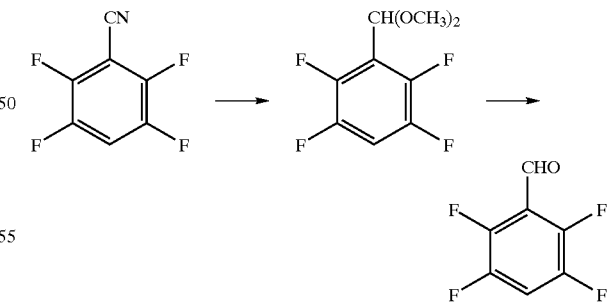

The same operation as in Example 9 was performed except for using 1.15 g of zinc sulfate and 8.26 g of sponge nickel having a water content of 6.31 g, and changing the time at the stirring in a hydrogen atmosphere to 7.5 hours. Before the distillation, the main products of the reaction solution were 2,3,5,6-tetrafluorobenzaldehyde and 2,3,5,6-tetrafluorobenzaldehyde dimethylacetal. After the distillation, 106.31 g of 2,3,5,6-tetrafluorobenzaldehyde having a purity of 99.9% was obtained as the main fraction oil layer (yield based on 2,3,5,6-tetrafluorobenzonitrile: 82.2 %).

Furthermore, it was found that 4.80 g of 2,3,5,6-tetrafluorobenzaldehyde was dissolved in the aqueous layer (yield based on 2,3,5,6-tetrafluorobenzonitrile: 3.7%).

EXAMPLE 12

Preparation of 2,3,5,6-Tetrafluorobenzaldehyde

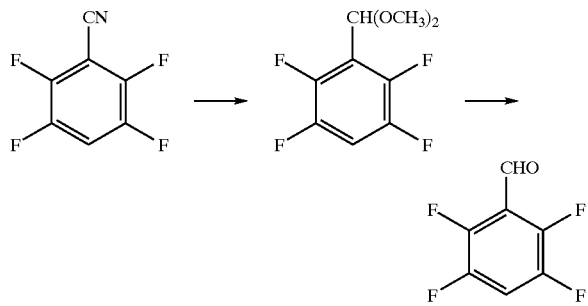

Into a 300 ml-volume glass-made autoclave, 25.03 g of 2,3,5,6-tetrafluorobenzonitrile and 69.70 g of methanol were charged. While stirring the mixture in a water bath, 29.38 g of 97% sulfuric acid was added dropwise. Subsequently, 1.33 g of sponge nickel having a water content of 1.17 g was added. After purging the vapor phase moiety with nitrogen, a pressure of 0.098 MPa (gauge pressure) was applied by hydrogen gas. While maintaining the pressure at 0.098 MPa, hydrogen was continuously supplied and the stirring was continued at 20° C. The amount of hydrogen absorbed was monitored by a mass flowmeter and after the passing of 4.5 hours, the absorption of hydrogen stopped. Thereafter, the vapor phase moiety was purged with nitrogen gas and the solution was stirred at 60° C. for 3 hours. The resulting reaction solution was analyzed by means of a gas chromatograph and it was confirmed that 2,3,5,6-tetrafluorobenzaldehyde and 2,3,5,6-tetrafluorobenzaldehyde dimethylacetal were mainly produced. After methanol was distilled off from the reaction solution, 70.2 g of water was added and the resulting solution was distilled under ordinary pressure. After cutting the first fraction containing methanol generated by the hydrolysis reaction of 2,3,5,6-tetrafluorobenzaldehyde dimethylacetal, 75.0 g of main fraction was allowed to distill. After standing at room temperature, the main fraction split into two layers of oil layer and aqueous layer. Thereafter, 19.75 g of oil layer was separated and cooled, then, the oil layer was crystallized. The crystal obtained was analyzed by means of a gas chromatograph as an internal standard method using o-dichlorobenzene and this compound was found to be 2,3,5,6-tetrafluorobenzaldehyde having a purity of 99.9%. In the analysis of gas chromatography, other impurities were not detected at all. The yield of 2,3,5,6-tetrafluorobenzaldehyde from 2,3,5,6-tetrafluorobenzonitrile was 78.83%. Also, the aqueous layer was analyzed by means of a gas chromatography and it was found that 0.88 g of 2,3,5,6-tetrafluorobenzaldehyde was dissolved therein (corresponding to a yield of 3.5% as calculated from 2,3,5,6-tetrafluorobenzonitrile).

EXAMPLE 13

Preparation of 2,3,5,6-Tetrafluorobenzaldehyde

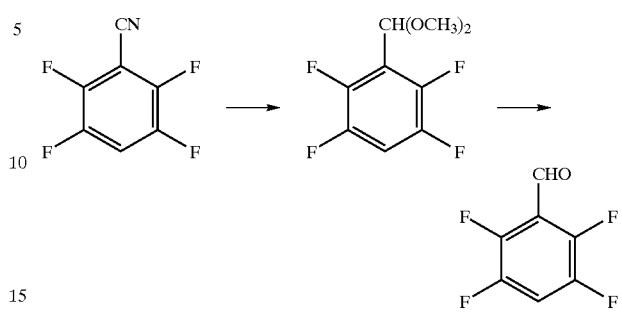

The same operation as Example 12 was performed except that the pressure applied by hydrogen was 0.059 MPa (gauge pressure) and the stirring was continued for 5 hours required until the absorption of hydrogen stopped. Before the distillation, the main products of the reaction solution were 2,3,5,6-tetrafluorobenzaldehyde and 2,3,5,6-tetrafluorobenzaldehyde dimethylacetal. After the distillation, 19.97 g of 2,3,5,6-tetrafluorobenzaldehyde having a purity of 99.9% was obtained as the main fraction oil layer (yield: 79.70%).

Furthermore, it was found that 0.80 g of 2,3,5,6-tetrafluorobenzaldehyde was dissolved in the aqueous layer (yield: 3.2%).

EXAMPLE 14

Preparation of Tetrafluoroterephthalaldehyde

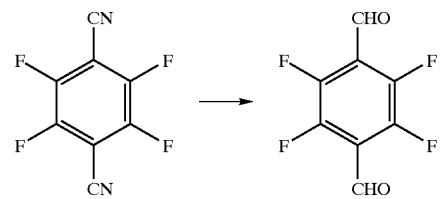

Into a 200 ml-volume glass-made reactor equipped with a condenser tube, 5.0 g of tetrafluoroterephthalonitrile and 67.5 g of methanol were charged, and stirring was started. The reactor inside was purged with nitrogen and while keeping the temperature at 25° C. by cooling with ice water, 11.0 g of 97% sulfuric acid was slowly added dropwise through a dropping funnel. Subsequently, 0.5g of sponge nickel was charged, the reactor was purged with hydrogen, a balloon charged with hydrogen gas was fixed to the reactor, and the solution was continuously stirred for 4 hours. Thereafter, the balloon charged with hydrogen gas was removed and after heating the reactor at a bath temperature of 80° C. for 1 hour, methanol was distilled off from the reaction solution by a rotary evaporator and 23.4 g of water was added to the residue. The resulting solution was heated under reflux at a bath temperature of 120° C. for 1 hour and then subjected to simple distillation under ordinary pressure. As a result, the objective tetrafluoroterephthalaldehyde was distilled with water. While adding water in an amount corresponding to the distilled amount through a dropping funnel, the distillation was continued until tetrafluoroterephthalaldehyde was not distilled. The distilled solution was dried to solidify by a rotary evaporator to obtain 1.83 g of 2,3,5,6-tetrafluoroterephthalaldehyde having a purity of 99% as a milky white crystal (yield: 35.5%).

EXAMPLE 15

Preparation of Tetrafluoroterephthalaldehyde

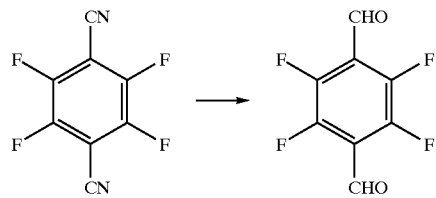

The same operation as in Example 14 was performed except for using 35.3 g of methanol and 10.3 g of 97% sulfuric acid, adding 1.0 g of copper acetate, and charging 0.7 g of sponge nickel. As a result, 2.96 g of tetrafluoroterephthalaldehyde having a purity of 99% was obtained as a milky white crystal (yield: 58.5%).

EXAMPLE 16

Preparation of Acetals of Tetrafluoroterephthalaldehyde and Tetrafluoroterephthalaldehyde

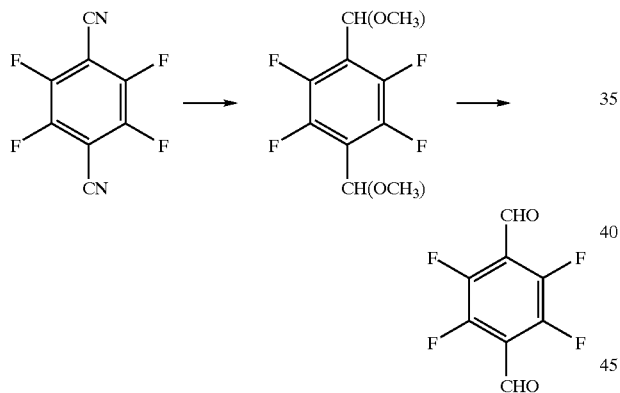

Into a 1 L-volume glass-made reactor equipped with a condenser tube, 50.0 g of tetrafluoroterephthalonitrile and 465.0 g of methanol were charged and stirring was started. The reactor inside was purged with nitrogen and while keeping the temperature at 25° C. by cooling with ice water, 103.0 g of 97% sulfuric acid was slowly added dropwise through a dropping funnel. Subsequently, 2.0 g of copper sulfate and 6.5 g of sponge nickel were charged. The reactor was purged with hydrogen, a balloon charged with hydrogen gas was fixed to the reactor, and the solution was continuously stirred for 8 hours at a temperature of 25±5° C. After the catalyst was filtered, methanol was distilled off by an evaporator. 300.0 g of water was added to the residue and crystals were precipitated at a room temperature. The crystals were filtered to obtain 47.6 g of tetrafluoroterephthalaldehyde acetal as a pale yellow crystal. Into a 300 mL-volume glass-made reactor equipped with a condenser tube, 140.0 g of the obtained tetrafluoroterephthalaldehyde acetal and 0.75 g of 97% sulfuric acid were charged. After heating and stirring the mixture at a temperature 100° C. for one hour, the methanol produced by hydrolysis reaction of acetal was distilled off under atmospheric pressure. The distillation was stopped when the highest temperature of the distillation reached 99° C., and crystals were precipitated until the reaction solution was cooled down to a room temperature while stirring. The crystal was filtered and dried under reduced pressure to obtain 23.1 g of tetrafluoroterephthalaldehyde having a purity of 99% (yield: 45%).

EXAMPLE 17

Preparation of 2,3,5,6-Tetrafluorobenzyl Alcohol

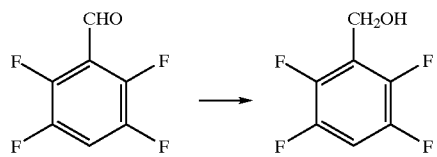

Into a 500 ml-volume stainless steel-made autoclave, 31.42 g of 2,3,5,6-tetrafluorobenzaldehyde having a purity of 99.9% obtained in Example 7 and 1.48 g of sponge nickel were charged. After purging with nitrogen, the reaction system was thoroughly purged with hydrogen gas to apply a pressure of 0.5 MPa (gauge pressure). While maintaining the pressure at 0.5 MPa, hydrogen was continuously supplied and the stirring was continued at 100° C. The amount of hydrogen absorbed was monitored by a mass flowmeter and after the passing of 269 minutes, the absorption of hydrogen stopped. The resulting reaction solution was analyzed by means of a gas chromatograph as an internal standard method using o-dichlorobenzene and it was found that the conversion of 2,3,5,6-tetrafluorobenzaldehyde was 100% and the yield of 2,3,5,6-tetrafluorobenzyl alcohol was 90.7% (based on 2,3,5,6-tetrafluorobenzaldehyde).

EXAMPLE 18

Preparation of 2,3,5,6-Tetrafluorobenzyl Alcohol

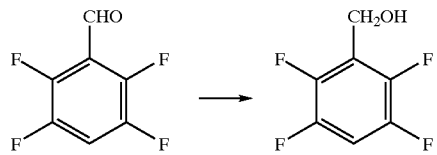

The same operation as in Example 17 was performed except for charging 88.25 g of 2,3,5,6-tetrafluorobenzaldehyde, 89.70 g of toluene and 2.69 g of sponge nickel. After 75 minutes passed, the absorption of hydrogen stopped. The resulting reaction solution was analyzed by means of a gas chromatograph as an internal standard method using o-dichlorobenzene and it was found that the conversion of 2,3,5,6-tetrafluorobenzaldehyde was 100% and the yield of 2,3,5,6-tetrafluorobenzyl alcohol was 99.3% (based on 2,3,5,6-tetrafluorobenzaldehyde).

The reaction solution obtained was distilled, then 85.77 g of 2,3,5,6-tetrafluorobenzyl alcohol having a purity of 99.8% was obtained.

EXAMPLE 19

Preparation of 2,3,5,6-Tetrafluorobenzenedimethanol

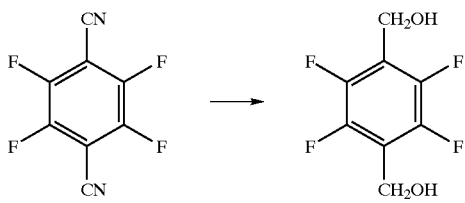

To a 100 ml-volume stainless steel-made autoclave, 5.92 g of tetrafluoroterephthalaldehyde having a purity of 99.9%, 28.66 g of 1,4-dioxane and 0.27 g of sponge nickel were charged. After purging with nitrogen, the system was thoroughly purged with hydrogen gas to apply a pressure of 0.5 MPa (gauge pressure). While maintaining the pressure at 0.5 MPa, hydrogen was continuously supplied and the stirring was continued at 100° C. The amount of hydrogen absorbed was monitored by a mass flowmeter and after the passing of 150 minutes, the absorption of hydrogen stopped. The resulting reaction solution was analyzed by means of a gas chromatograph as an internal standard method using o-dichlorobenzene and it was found that the conversion of tetrafluoroterephthalaldehyde was 100% and the yield of 2,3,5,6-tetrafluorobenzenedimethanol was 87.3%. From the reaction solution, the catalyst was filtered and 1,4-dioxane was distilled off by a rotary evaporator, then, a white solid was obtained. To the solid obtained, 30 g of toluene was added. The resulting mixture was heated under reflux for 30 minutes, cooled and then filtered to obtain 5.30 g of 2,3,5,6-tetrafluorobenzenedimethanol having a purity of 93.4% was obtained as a white crystal.

Comparative Example 1

Preparation of 2,3,5,6-Tetrafluorobenzaldehyde not via Producing Acetals

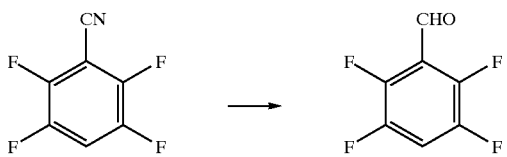

Into a 500 ml-volume glass-made reactor equipped with a condenser tube, 5.00 g of 2,3,5,6-tetrafluorobenzonitrile, 51.00 g of methanol, 52.00 g of water, 45.00 g of acetic acid and 0.50 g of sponge nickel were charged. After purging the vapor phase moiety with hydrogen gas, the mixed solution was stirred at 60° C. under atmospheric pressure while continuously supplying hydrogen. As the time passed, the reaction solution was sampled and analyzed by means of a gas chromatograph. As a result, it was confirmed that 2,3,5,6-tetrafluorobenzyl alcohol was produced together with 2,3,5,6-tetrafluorobenzaldehyde. The yields in the reaction solution are shown in the table below.

| Reaction Time (min.) | Yield of Benzaldehyde (%) | Yield of Benzyl Alcohol (%) |
|---|---|---|
| 80 | 63.4 | 0.2 |
| 120 | 84.0 | 0.8 |
| 180 | 65.3 | 7.8 |

The yield reached the maximum value after 120 minutes but thereafter, abruptly decreased.

INDUSTRIAL APPLICABILITY

According to the present invention, tetrafluorobenzenemethanols represented by formula (4), tetrafluorobenzenecarbaldehydes represented by formula (3) and tetrafluorobenzenecarbaldehyde dimethylacetals represented by formula (5) can be produced in a high purity and a high yield by an industrially advantageous method. In particular, 2,3,5,6-tetrafluorobenzyl alcohol, 2,3,5,6-tetraflourobenzenedimethanol, 2,3,5,6-tetrafluorobenzaldehyde, 2,3,5,6-tetrafluoroterephthalaldehyde, 2,3,5,6-tetrafluoroterephthalaldehyde dimethylacetal and 2,3,5,6-tetrafluobenzaldehyde dimethylacetal, which are useful as an intermediate in the production of pyrethroids having good insecticidal action and at the same time exhibiting low toxicity to human body, can be produced in a high purity and a high yield.

What is claimed is:

1. A process for producing a tetrafluorobenzenecarbaldehyde dialkylacetal represented by formula (2):

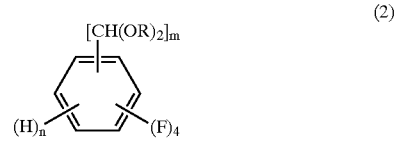

(2)

wherein m represents 1 or 2, n represents 0 or 1, and m+n=2, comprising catalytically reducing a tetrafluorocyanobenzene represented by formula (1)

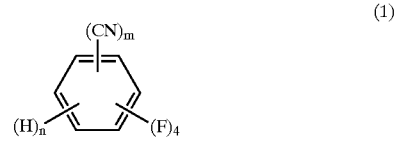

(1)

in the presence of an alkyl alcohol represented by R—OH, wherein R represents an alkyl group having from 1 to 4 carbon atoms, and an acid, and wherein copper, tin, molybdenum, or zinc as a dissimilar metal component is added to a catalyst used in the catalytic reduction.

2. The process for producing a tetrafluorobenzenecarbaldehyde dialkylacetal as described in claim 1, wherein the alkyl alcohol is methanol and the compound represented by formula (2) is tetrafluorobenzenecarbaldehyde dimethylacetal.

3. The process for producing a tetrafluorobenzenecarbaldehyde dialkylacetal as claimed in claim 1, wherein the catalyst used in the catalytic reduction is sponge nickel.

4. The process for producing a tetrafluorobenzenecarbaldehyde dialkylacetal as claimed in claim 1, wherein the catalytic reduction is carried out under condition that the amount of water present in the reaction is 1 time in mol or less based on the acetal group of tetrafluorobenzenecarbaldehyde dialkylacetal represented by formula (2).

5. A process for producing a tetrafluorobenzenecarbaldehyde represented by formula (3)

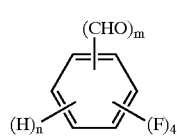

(3)

wherein m represents 1 or 2, n represents 0 or 1, and m+n=2, comprising adding water and then hydrolyzing a tetrafluorobenzenecarbaldehyde dialkylacetal represented by formula (2)

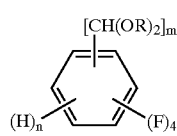

(2)

wherein m and n have the same meanings as defined above and R represents an alkyl group having from 1 to 4 carbon atoms, while separating an alkyl alcohol by distillation.

6. A process for producing a tetrafluorobenzenecarbaldehyde claimed in claim 5 using fluorobenzenecarbaldehyde dialkylacetal represented by formula (2)

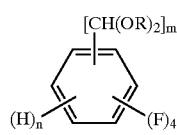

(2)

obtained by catalytically reducing a tetrafluorocyanobenzene represented by formula (1)

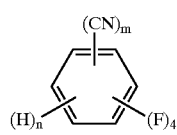

(1)

wherein m represents 1 or 2, n represents 0 or 1, and m+n=2, in the presence of an alkyl alcohol represented by R—OH wherein R is an alkyl group having 1 to 4 carbon atoms, and an acid.

7. A process for producing a tetrafluorobenzenecarbaldehyde represented by formula (3)

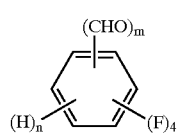

(3)

wherein m represents 1 or 2, n represents 0 or 1, and m+n=2, comprising adding water and then hydrolyzing a tetrafluorobenzenecarbaldehyde dialkylacetal represented by formula (2)

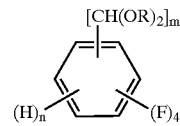

(2)

wherein m and n have the same meanings as defined above and R represents an alkyl group having from 1 to 4 carbon atoms, while separating an alkyl alcohol by distillation, wherein formula (2) is obtained by catalytically reducing a tetrafluorocyanobenzene represented by formula (1)

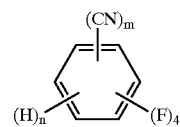

(1)

wherein m and n have the same meanings as defined above, in the presence of an alkyl alcohol represented by R—OH wherein R has the same meaning as above, and an acid.

8. The process for producing a tetrafluorobenzenecarbaldehyde as described in claim 5 or 7 wherein water in excess amount of 10 times in mol or more is used based on the acetal group of tetrafluorobenzenecarbaldehyde dialkylacetal represented by formula (2).

9. The process for producing a tetrafluorobenzenecarbaldehyde as described in any one of claims 5 to 7, wherein the tetrafluorobenzenecarbaldehyde dialkylacetal represented by formula (2) is 2,3,5,6-tetrafluorobenzaldehyde dialkylacetal or 2,3,5,6-tetrafluoroterephthalaldehyde dialkylacetal, and the tetrafluorobenzenecarbaldehyde represented by formula (3) is corresponding 2,3,5,6-tetrafluorobenzaldehyde or 2,3,5,6-tetrafluoroterephthalaldehyde.

10. A process for producing a tetrafluorobenzenemethanol represented by formula (4),

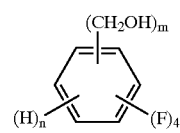

(4)

m represents 1 or 2, n represents 0 or 1, and m+n=2, comprising adding water and hydrolyzing a tetrafluorobenzenecarbaldehyde dialkylacetal represented by formula (2)

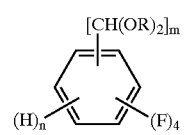

(2)

wherein m and n have the same meanings as defined above and R represents an alkyl group having from 1 to 4 carbon atoms, while separating an alkyl alcohol by distillation to obtain a tetrafluorobenzenecarbaldehyde represented by formula (3), and reducing the tetrafluorobenzenecarbaldehyde represented by formula (3)

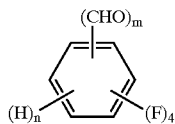
(3)

wherein m and n have the same meanings as defined above to produce the tetrafluorobenzenemethanol represented by formula (4).

11. The process for producing a tetrafluorobenzenemethanol as claimed in claim 10, wherein the tetrafluorobenzenecarbaldehyde dialkylacetal represented by formula (2) is 2,3,5,6-tetrafluorobenzaldehyde dialkylacetal or 2,3,5,6-tetrafluoroterephthalaldehyde dialkylacetal, the tetrafluorobenzenecarbaldehyde represented by formula (3) is corresponding 2,3,5,6-tetrafluorobenzaldehyde or 2,3,5,6-tetrafluoroterephthalaldehyde, and the tetrafluorobenzenemethanol represented by formula (4) is corresponding 2,3,5,6-tetrafluorobenzyl alcohol or 2,3,5,6-tetrafluorobenzenedimethanol.

12. The process for producing a tetrafluorobenzenecarbaldehyde as described in claim 5, wherein the tetrafluorobenzenecarbaldehyde dialkylacetal is produced by a process comprising catalytically reducing a tetra-fluorocyanobenzene represented by formula (1)

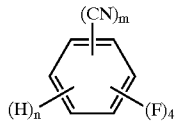
(1)

in the presence of an alkyl alcohol represented by R—OH, wherein R represents an alkyl group having from 1 to 4 carbon atoms, and an acid, and wherein copper, tin, molybdenum, or zinc as a dissimilar metal component is added to a catalyst used in the catalytic reduction.

13. The process for producing a tetrafluorobenzenecarbaldehyde as described in claim 7, wherein copper, tin, molybdenum, or zinc as a dissimilar metal component is added to a catalyst used in the catalytic reduction.

14. The process for producing a tetrafluorobenzenecarbaldehyde as described in claim 12 or 13, wherein water in excess amount of 10 times in mol or more is used based on the acetal group of tetrafluorobenzenecarbaldehyde dialkylacetal represented by formula (2).

15. The process for producing a tetrafluorobenzenecarbaldehyde as described in claim 12 or 13, wherein the tetrafluorobenzenecarbaldehyde dialkylacetal represented by formula (2) is 2,3,5,6-tetrafluorobenzaldehyde dialkylacetal or 2,3,5,6-tetrafluoroterephthalaldehyde dialkylacetal, and the tetrafluorobenzenecarbaldehyde represented by formula (3) is corresponding 2,3,5,6-tetrafluorobenzaldehyde or 2,3,5,6-tetrafluoroterephthalaldehyde.

16. The process for producing a tetrafluorobenzenemethanol as described in claim 10, wherein the tetrafluorobenzenecarbaldehyde dialkylacetal is produced by a process comprising catalytically reducing a tetra-fluorocyanobenzene represented by formula (1)

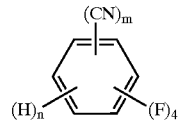
(1)

in the presence of an alkyl alcohol represented by R—OH, wherein R represents an alkyl group having from 1 to 4 carbon atoms, and an acid, and wherein copper, tin, molybdenum, or zinc as a dissimilar metal component is added to a catalyst used in the catalytic reduction.

17. The process for producing a tetrafluorobenzenemethanol as described in claim 11, wherein the tetrafluorobenzenecarbaldehyde dialkylacetal is produced by a process comprising catalytically reducing a tetra-fluorocyanobenzene represented by formula (1)

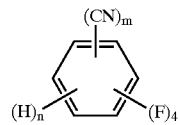
(1)

in the presence of an alkyl alcohol represented by R—OH, wherein R represents an alkyl group having from 1 to 4 carbon atoms, and an acid, and wherein copper, tin, molybdenum, or zinc as a dissimilar metal component is added to a catalyst used in the catalytic reduction.

* * * * *